(12) United States Patent
Azorsa

(10) Patent No.: US 9,611,319 B2
(45) Date of Patent: Apr. 4, 2017

(54) HYBRIDOMA CLONES AND MONOCLONAL ANTIBODIES TO FIBROBLAST GROWTH FACTOR 4

(71) Applicant: The Translational Genomics Research Institute, Phoenix, AZ (US)

(72) Inventor: David Azorsa, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 14/774,083

(22) PCT Filed: Mar. 12, 2014

(86) PCT No.: PCT/US2014/025097
§ 371 (c)(1),
(2) Date: Sep. 9, 2015

(87) PCT Pub. No.: WO2014/165287
PCT Pub. Date: Oct. 9, 2014

(65) Prior Publication Data
US 2016/0017027 A1    Jan. 21, 2016

Related U.S. Application Data

(60) Provisional application No. 61/777,720, filed on Mar. 12, 2013.

(51) Int. Cl.
| | | |
|---|---|---|
| A61K 39/395 | (2006.01) |
| C12N 5/07 | (2010.01) |
| C07K 16/28 | (2006.01) |
| C07K 16/22 | (2006.01) |
| C12N 5/16 | (2006.01) |

(52) U.S. Cl.
CPC .......... *C07K 16/22* (2013.01); *C07K 16/2863* (2013.01); *C12N 5/163* (2013.01)

(58) Field of Classification Search
None
See application file for complete search history.

(56) References Cited

U.S. PATENT DOCUMENTS

| | | |
|---|---|---|
| 2010/0169992 A1 | 7/2010 | Bange |
| 2011/0150903 A1 | 6/2011 | Baurin |

FOREIGN PATENT DOCUMENTS

| | | |
|---|---|---|
| JP | 2010-508037 | 3/2010 |
| JP | 2011-527322 | 10/2011 |
| JP | 2012-501637 | 1/2012 |
| WO | WO 2012/138975 | 10/2012 |

*Primary Examiner* — Marianne P Allen
(74) *Attorney, Agent, or Firm* — Rodney J. Fuller; Booth Udall Fuller, PLC

(57) ABSTRACT

The present invention is directed to a monoclonal antibody that recognizes human FGFR4 in its native form. The invention is also directed to a hybridoma cell line that produces the monoclonal antibody and methods of use thereof.

7 Claims, 3 Drawing Sheets

SEQUENCE LISTING

<160> NUMBER OF SEQ ID NOS: 2

<210> SEQ ID NO 1
<211> LENGTH: 802
<212> TYPE: PRT
<213> ORGANISM: Homo sapiens

<400> SEQUENCE: 1

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala

```
                35                  40                  45
Leu Gly Gln Pro Val Arg Leu Cys Cys Gly Arg Ala Glu Arg Gly Gly
 50                  55                  60
His Trp Tyr Lys Glu Gly Ser Arg Leu Ala Pro Ala Gly Arg Val Arg
 65                  70                  75                  80
Gly Trp Arg Gly Arg Leu Glu Ile Ala Ser Phe Leu Pro Glu Asp Ala
                 85                  90                  95
Gly Arg Tyr Leu Cys Leu Ala Arg Gly Ser Met Ile Val Leu Gln Asn
                100                 105                 110
Leu Thr Leu Ile Thr Gly Asp Ser Leu Thr Ser Ser Asn Asp Asp Glu
                115                 120                 125
Asp Pro Lys Ser His Arg Asp Pro Ser Asn Arg His Ser Tyr Pro Gln
130                 135                 140
Gln Ala Pro Tyr Trp Thr His Pro Gln Arg Met Glu Lys Lys Leu His
145                 150                 155                 160
Ala Val Pro Ala Gly Asn Thr Val Lys Phe Arg Cys Pro Ala Ala Gly
                165                 170                 175
Asn Pro Thr Pro Thr Ile Arg Trp Leu Lys Asp Gly Gln Ala Phe His
                180                 185                 190
Gly Glu Asn Arg Ile Gly Gly Ile Arg Leu Arg His Gln His Trp Ser
                195                 200                 205
Leu Val Met Glu Ser Val Val Pro Ser Asp Arg Gly Thr Tyr Thr Cys
210                 215                 220
Leu Val Glu Asn Ala Val Gly Ser Ile Arg Tyr Asn Tyr Leu Leu Asp
225                 230                 235                 240
Val Leu Glu Arg Ser Pro His Arg Pro Ile Leu Gln Ala Gly Leu Pro
                245                 250                 255
Ala Asn Thr Thr Ala Val Val Gly Ser Asp Val Glu Leu Leu Cys Lys
                260                 265                 270
Val Tyr Ser Asp Ala Gln Pro His Ile Gln Trp Leu Lys His Ile Val
                275                 280                 285
Ile Asn Gly Ser Ser Phe Gly Ala Asp Gly Phe Pro Tyr Val Gln Val
                290                 295                 300
Leu Lys Thr Ala Asp Ile Asn Ser Ser Glu Val Glu Val Leu Tyr Leu
305                 310                 315                 320
Arg Asn Val Ser Ala Glu Asp Ala Gly Glu Tyr Thr Cys Leu Ala Gly
                325                 330                 335
Asn Ser Ile Gly Leu Ser Tyr Gln Ser Ala Trp Leu Thr Val Leu Pro
                340                 345                 350
Glu Glu Asp Pro Thr Trp Thr Ala Ala Pro Glu Ala Arg Tyr Thr
                355                 360                 365
Asp Ile Ile Leu Tyr Ala Ser Gly Ser Leu Ala Leu Ala Val Leu Leu
                370                 375                 380
Leu Leu Ala Gly Leu Tyr Arg Gly Gln Ala Leu His Gly Arg His Pro
385                 390                 395                 400
Arg Pro Pro Ala Thr Val Gln Lys Leu Ser Arg Phe Pro Leu Ala Arg
                405                 410                 415
Gln Phe Ser Leu Glu Ser Gly Ser Gly Lys Ser Ser Ser Ser Leu
                420                 425                 430
Val Arg Gly Val Arg Leu Ser Ser Ser Gly Pro Ala Leu Leu Ala Gly
                435                 440                 445
Leu Val Ser Leu Asp Leu Pro Leu Asp Pro Leu Trp Glu Phe Pro Arg
450                 455                 460
```

-continued

```
Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
            485                 490                 495

Ala Ser Thr Val Ala Val Lys Met Leu Lys Asp Asn Ala Ser Asp Lys
        500                 505                 510

Asp Leu Ala Asp Leu Val Ser Glu Met Glu Val Met Lys Leu Ile Gly
    515                 520                 525

Arg His Lys Asn Ile Ile Asn Leu Leu Gly Val Cys Thr Gln Glu Gly
530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
        595                 600                 605

Ile His Arg Asp Leu Ala Ala Arg Asn Val Leu Val Thr Glu Asp Asn
    610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu
    690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
        755                 760                 765

Gly Asp Ala Ser Ser Thr Cys Ser Ser Ser Asp Ser Val Phe Ser His
    770                 775                 780

Asp Pro Leu Pro Leu Gly Ser Ser Phe Pro Phe Gly Ser Gly Val
785                 790                 795                 800

Gln Thr

<210> SEQ ID NO 2
<211> LENGTH: 348
<212> TYPE: PRT
<213> ORGANISM: Homo sapiens
```

```
<400> SEQUENCE: 2

Leu Glu Ala Ser Glu Glu Val Glu Leu Glu Pro Cys Leu Ala Pro Ser
1               5                   10                  15

Leu Glu Gln Gln Glu Gln Leu Thr Val Ala Leu Gly Gln Pro Val
            20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
        210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu Ala Arg Tyr Thr Asp
            340                 345
```

HYBRIDOMA CLONES AND MONOCLONAL ANTIBODIES TO FIBROBLAST GROWTH FACTOR 4

CROSS-REFERENCE TO RELATED APPLICATIONS

The present application is the national stage of International Patent Application No. PCT/US2014/025097, filed on Mar. 12, 2014, which claims priority to U.S. Application No. 61/777,720, filed Mar. 12, 2013, the entire contents and disclosure of which are herein incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 11 kilobyte ASCII (text) file named "FGFR4Seq371 List" created on Sep. 9, 2015.

FIELD OF THE INVENTION

This invention relates to hybridoma clones and monoclonal antibodies, and more particularly, hybridoma clones and monoclonal antibodies directed to fibroblast growth factor receptor 4 (FGFR4) and methods of use.

BACKGROUND OF THE INVENTION

The fibroblast growth factor (FGF) family is composed of structurally related polypeptides that bind to 4 receptor tyrosine kinases (Fibroblast Growth Factor Receptors 1-4) and one kinase deficient receptor (Fibroblast Growth Factor Receptor 5) (Eswarakumar et al. (2005) Cytokine Growth Factor Rev 16:139; Ornitz et al. (2001) Genome Biol 2:3005.1; Sleeman et al. (2001) Gene 271:171). The FGF receptors can be activated by the FGF family, which includes 23 unique members to date (Eswarakumar et al. (2005) Cytokine Growth Factor Rev 16:139; Yamashita, T. (2005) Therapeutic Apheresis and Dialysis, 9:313). In contrast to Fibroblast Growth Factor Receptor 4, where only two splice variants are known, other family members such as Fibroblast Growth Factor Receptors 1-3 can be altered in their affinity for different FGFs by multiple splice variations (van Heumen et al. (1999) IUBMB Life 48:73).

Fibroblast growth factor receptors (FGFRs) are of great interest in cancer biology as these receptors regulate essential processes including cellular survival, motility, development, and angiogenesis. In humans, FGFRs have a highly conserved amino acid sequence across family members, including FGFR1, FGFR2, FGFR3, and FGFR4. These cell surface receptors include extracellular immunoglobulin-like domains, a transmembrane domain, and an intracellular tyrosine kinase (TK) domain. The interaction of FGFs with FGFR1-4 results in receptor homodimerization and autophosphorylation, recruitment of cytosolic adaptors such as FRS2 and initiation of multiple signaling pathways (Powers et al. (2000) Endocr Relat Cancer 7:165; Schlessinger, J. (2004) Science 306:1506).

FGFR4 is activated by FGF1, FGF2, FGF4, FGF6, FGF8 and FGF9 with decreasing efficiency, respectively (Ornitz et al. (1996) J. Biol. Chem. 271:15292). Although each of these FGFs also activates other FGFR family members, FGF19 is specific for FGFR4 (Xie et al. (1999) Cytokine JID-9005353 11:729). Activation of FGFR4 by FGFs requires binding of the ligand to heparin; although, FGFR4 can also be activated by heparin alone (Gao and Goldfarb, (1995) EMBO J. 14:2183). Many FGFs are broad-spectrum mitogens, whereas some induce cell motility, or alter the state of cellular differentiation (McKeehan et al. (1998) Prog Nucleic Acid Res Mol. Biol 59:135). In vivo, some FGFs have potent angiogenic properties, and others have been implicated in tissue remodeling, including wound repair (Werner et al., (1994) Science 266:819).

Upon binding of a ligand to the extracellular domain of FGFR4, this receptor dimerizes, which results in the phosphorylation of residues in the TK domain. This phosphorylation induces the recruitment of signaling molecules to the intracellular domain, thereby activating one or more signaling pathways (Vainikka et al. (1992) EMBO J 11:4273; Vainikka et al. (1994) J. Biol. Chem. 269:18320). For example, FGFR4 associates with PLC-γ1, and an increase in MAP kinase activation and DNA synthesis upon FGF stimulation has been observed. Further interaction with other human FGFR family members may expand the signaling potential of FGFR4 and can provide not only signal diversification, but also signal amplification (McKeehan & Kan (1994) Mol Reprod Dev 39:69). An 85-kDa serine kinase has been found to negatively regulate tyrosine phosphorylation of FGFR4, but its exact function has not been elucidated (Vainikka et al. (1996) J Biol Chem 271:1270). Association of FGFR4 with NCAM has been demonstrated to mediate integrin-dependent adhesion (Cavallaro et al. (2001) Nat Cell Biol 3:650), which might play a decisive role in tumor metastasis.

FGFs and FGFRs play important roles in development and tissue repair by regulating cell proliferation, migration, chemotaxis, differentiation, morphogenesis and angiogenesis (Ornitz et al. (2001) Genome Biol 2:3005.1; Auguste et al. (2003) Cell Tissue Res 314:157; Steiling et al. (2003) Curr Opin Biotechnol 14:533). Several FGFs and FGFRs are associated with the pathogenesis of breast, prostate, cervical, stomach, and colon cancers (Jeffers et al. (2002) Expert Opin Ther Targets 6:469; Mattila et al. (2001) Oncogene 20:2791-2; Ruohola et al. (2001) Cancer Res 61:4229; Marsh et al. (1999) Oncogene 18:1053; Shimokawa et al. (2003) Cancer Res 63:6116; Jang (2001) Cancer Res 61:3541; Cappellen (1999) Nat Genet 23:18; Gowardhan (2005) Br J Cancer 92:320).

In addition, FGFR4 expression is widely distributed and was reported in tissues including developing skeletal muscles, liver, lung, pancreas, adrenal, kidney, and brain (Kan et al. (1999) J Biol Chem 274:15947; Nicholes et al. (2002) Am J Pathol 160:2295; Ozawa et al. (1996) Brain Res Mol Brain Res 41:279; Stark et al. (1991) Development 113:641). FGFR4 amplification was reported in mammary and ovarian adenocarcinomas (Jaakkola et al. (1993) Int J Cancer 54:378). Moreover, mutations and truncations of FGFR4 have correlated with malignancy, and in some cases, the prognosis of prostate and lung adenocarcinomas, head and neck squamous cell carcinoma, soft tissue sarcoma, astrocytoma and pituitary adenomas (Jaakkola et al. (1993) Int J Cancer 54:378; Morimoto (2003) Cancer 98:2245; Qian (2004) J Clin Endocrinol Metab 89:1904; Spinola et al. (2005) J Clin Oncol 23:7307; Streit et al. (2004) Int J Cancer 111:213; Wang (1994) Mol Cell Biol 14:181; Yamada (2002) Neurol Res 24:244). In addition, a polymorphism at amino acid 388 of the polypeptide sequence of FGFR4 is associated with a more aggressive disease status in melanoma (Streit al al., 2006), breast (Bange et al, 2002), prostate (Wang et al. (2004) Clin Cancer Res. 10:6169), head and neck squamous cell carcinomas (HNSCC) (Streit et al.

(2004) Int J Cancer 111:213), lung adenocarcinoma (Spinola et al. (2005) J Clin Oncol 23:7307) and soft tissue sarcoma (Morimoto et al. (2003) Cancer 98:2245).

Interestingly, transgenic expression of an FGFR4 specific ligand, FGF19, under control of a muscle-specific promoter in mice has been found to lead to hepatocellular carcinoma (Nicholes et al. (2002) Am J Pathol 160:2295).

Accordingly, agents that specifically target FGFR4 and/or interfere with FGFR4-mediated signaling are desirable. Anti-FGFR4 antibodies with unique genetic and amino acid structures, including unique binding and functional characteristics, are particularly useful. Such antibodies may serve as diagnostic and therapeutic tools for a variety of diseases, including cancer.

SUMMARY

Some embodiments of the invention include antibodies and fragments thereof that bind to FGFR4. The invention is also directed to one or more hybridoma cell lines that produce the one or more antibodies that specifically bind to FGFR4, and to methods of using the antibodies. In some embodiments, the antibodies are monoclonal antibodies. Moreover, in some embodiments, the monoclonal antibodies recognize the native, non-reduced FGFR4 polypeptide.

Some embodiments of the invention include antibodies and fragments thereof that bind to native FGFR4 polypeptide or a fragment thereof. For example, at least some of the antibodies specifically bind to a FGFR4 polypeptide of SEQ ID NO:1. In other aspects, at least some of the antibodies binds to FGFR4 polypeptides or fragments thereof that comprise SEQ ID NO:2.

The antibodies of the present invention are preferably isolated monoclonal antibodies having specific binding properties against a human FGFR4 protein, more preferably against human FGFR4 in its native, non-reduced form. The antibodies may be labeled with one or more labels selected from the group consisting of a biotin label, a fluorescent label, an enzyme label, a coenzyme label, a chemiluminescent label, and a radioactive isotope label.

Some embodiments of the invention include a monoclonal antibody that is produced by one or more hybridoma cell lines. For example, the invention includes a monoclonal antibody comprising the same epitope specificity as a monoclonal antibody produced by hybridoma cell line BT53, which has been deposited with the ATCC.

Some embodiments of the invention include a method of making a monoclonal antibody that includes providing hybridoma cell line BT53. This hybridoma cell line can produce a monoclonal antibody that is specific for human FGFR4. In some aspects, the method includes culturing the hybridoma cell line BT53 under conditions that permit the production of the monoclonal antibody.

Additional objectives, advantages and novel features will be set forth in the description which follows or will become apparent to those skilled in the art upon examination of the drawings and detailed description which follows.

BRIEF DESCRIPTION OF THE DRAWINGS

Illustrative and exemplary embodiments of the invention are shown in the drawings in which.

DETAILED DESCRIPTION OF THE INVENTION

Figure 1:
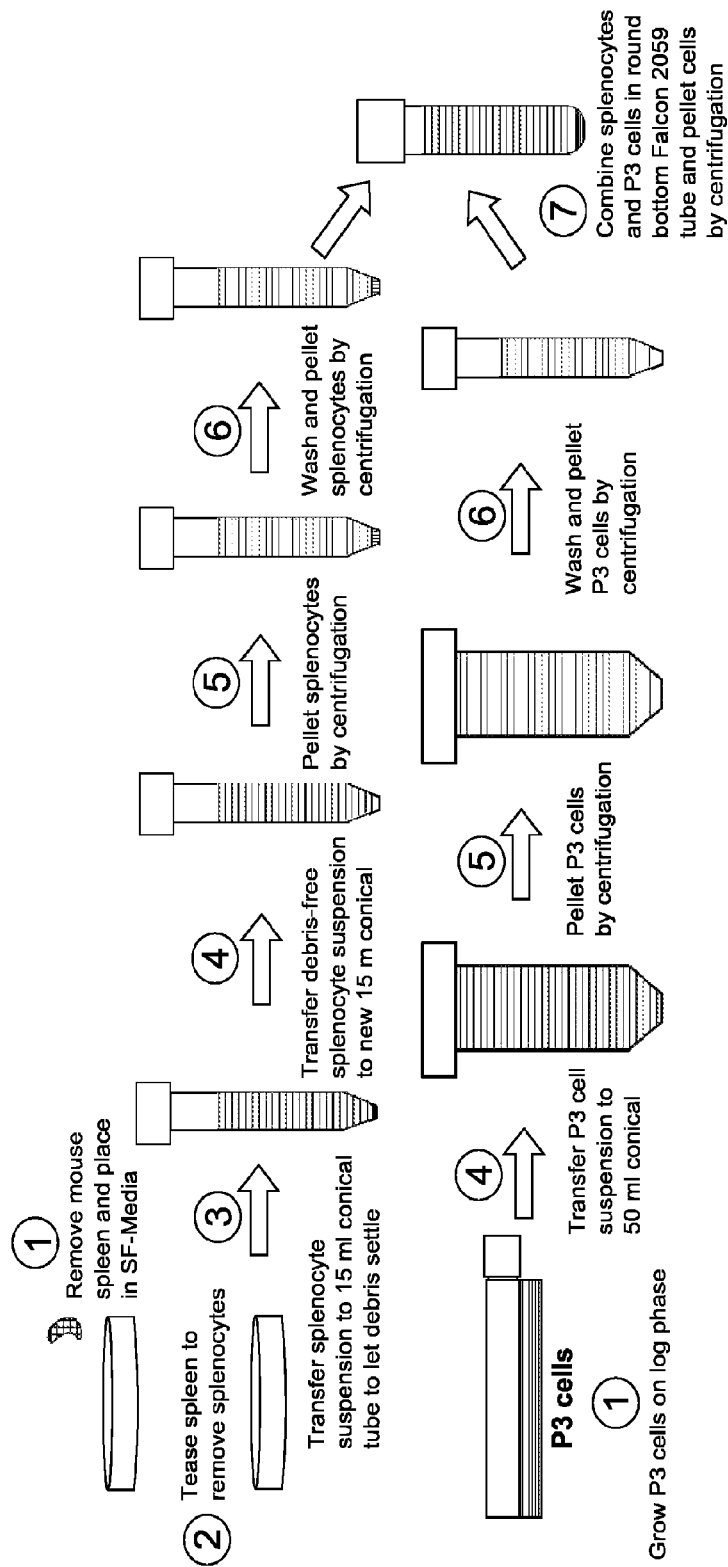
FIG. 1 illustrates the steps taken to produce hybridomas disclosed herein.

The present invention is directed to an antibody that recognizes human fibroblast growth factor receptor 4 (FGFR4). The invention is also directed to a hybridoma cell line that produces the antibody, and to methods of using the antibody. More specifically, the inventors produced a murine hybridoma clone that secretes murine monoclonal antibodies to the human FGFR4 protein that are designated BT53. The anti-FGFR4 monoclonal antibodies recognize human FGFR4 in its native form. In some embodiments of the invention, the anti-FGFR4 monoclonal antibody recognizes native human FGFR4 in its native, non-reduced form.

The term "antibody" is used herein in the broadest sense and refers generally to a molecule that contains at least one antigen binding site that immunospecifically binds to a particular antigen target of interest. The term "antibody" thus includes but is not limited to native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. The term "antibody," thus, includes full length antibodies and/or their variants, as well as fragments thereof. Binding of an antibody to a target can cause a variety of effects, such as but not limited to where such binding modulates, decreases, increases, antagonizes, agonizes, mitigates, alleviates, blocks, inhibits, abrogates and/or interferes with at least one target activity or binding, or with receptor activity or binding, in vitro, in situ, and/or in vivo. The present invention, thus, encompasses antibody fragments capable of binding to a biological molecule (such as an antigen or receptor) or portions thereof, including but not limited to Fab, Fab' and F(ab')$_2$, facb, pFc', Fd, Fv or scFv fragments. (See, e.g., CURRENT PROTOCOLS IN IMMUNOLOGY, (Colligan et al. eds., John Wiley & Sons, Inc., NY, 1994-2001)); diabodies; linear antibodies (Zapata et al. (1995) Protein Eng. 8(10):1057); single-chain antibody molecules; and multispecific antibodies formed from antibody fragments.

Accordingly, antibody is used in the broadest sense and specifically covers, for example, single anti-FGFR4 monoclonal antibodies (including agonist, antagonist, and neutralizing antibodies), anti-FGFR4 antibody compositions with polyepitopic specificity, single chain anti-FGFR4 antibodies, and fragments of anti-FGFR4 antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibody may be abbreviated "mAb."

"Fv" is the minimum antibody fragment that contains a complete antigen-recognition and antigen-binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) of any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. Preferably, the Fv polypeptide further comprises a polypeptide linker between the $V_H$ and $V_L$ domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) Proc. Natl. Acad. Sci. USA 90:6444.

An "isolated" antibody is one that has been identified and separated and/or recovered from a component of its natural environment. Contaminant components of its natural environment are materials, which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "native sequence FGFR4 polypeptide" or "native sequence FGFR4 protein" comprises a polypeptide having the same amino acid sequence as the corresponding FGFR4 polypeptide derived from nature. Such native sequence FGFR4 polypeptides can be isolated from nature or can be produced by recombinant or synthetic methods. The term "native sequence FGFR4 polypeptide" specifically encompasses naturally-occurring truncated, secreted, and/or membrane-bound forms of the specific FGFR4 polypeptide, naturally-occurring variant forms (e.g., alternatively spliced forms) and naturally-occurring allelic variants of the polypeptide. In various embodiments of the invention, the native sequence FGFR4 polypeptides disclosed herein are mature or full-length native sequence polypeptides comprising the full-length amino acid sequences recited herein. In some embodiments, the "native sequence FGFR4 polypeptide" comprises an amino acid sequence of SEQ ID NO:1 or a fragment thereof. Moreover, in some embodiments, the "native sequence FGFR4 polypeptide" comprises a fragment of the full-length polypeptide or protein, such as an amino acid of SEQ ID NO:2.

The terms "individual," "subject," and "patient," used interchangeably herein, refer to an animal, preferably a mammalian (including a non-primate and a primate), including, but not limited to, murines, simians, humans, mammalian farm animals (e.g., bovine, porcine, ovine), mammalian sport animals (e.g., equine), and mammalian pets (e.g., canine and feline); preferably the term refers to humans.

As used herein, the terms "treatment", "treating", and the like, refer to obtaining a desired pharmacologic, and/or physiologic effect. The effect may be therapeutic in terms of a partial or complete cure for a disease and/or adverse effect attributable to the disease. "Treatment," as used herein, includes administration of a compound of the present invention for treatment of a disease or condition in a mammal, particularly in a human, and includes: (a) inhibiting the disease, i.e., arresting its development; (b) providing palliative care, i.e., reducing and preventing the suffering of a patient; and (c) relieving the disease, i.e., causing regression of the disease or disorder or alleviating symptoms or complications thereof. Dosage regimens may be adjusted to provide the optimum desired response.

As used herein, the term "epitope" refers to a portion of an antigenic molecule to which an antibody is produced and to which the antibody will bind. A "FGFR4 epitope" comprises the part of the FGFR4 protein to which an anti-FGFR4 monoclonal antibody specifically binds. Epitopes can comprise linear amino acid residues (i.e., residues within the epitope are arranged sequentially one after another in a linear fashion), nonlinear amino acid residues, or both linear and nonlinear amino acid residues. Typically epitopes are generally short amino acid sequences (e.g. about five amino acids in length).

Monoclonal Antibodies

The anti-FGFR4 antibodies may, alternatively, be monoclonal antibodies. Monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

An immunizing agent typically includes the FGFR4 polypeptide, a portion thereof, a fusion protein thereof, and/or a whole cell (i.e., fixed or living cell) or fragment of a cell that expresses FGFR4. For example, human platelets are known to express FGFR4 such that fixed human platelets can be used as the immunizing agent. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding (1986) Monoclonal Antibodies: Principles and Practice, Academic Press, pp. 59-103). Immortalized cell lines may be transformed mammalian cells, particularly myeloma cells of rodent, bovine, and human origin. Rat or mouse myeloma cell lines may be employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor (1984) J. Immunol. 133:3001; Brodeuretal (1987) Monoclonal Antibody Production Techniques and Applications, Marcel Dekker, Inc., New York, pp. 51-631).

The culture medium in which the hybridoma cells are cultured can then be assayed for the presence of monoclonal antibodies directed against FGFR4 or a fragment thereof. The binding specificity of monoclonal antibodies produced by the hybridoma cells can be determined by inmunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard (1980) Anal. Biochem. 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures, such as, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof can be accomplished using routine techniques known in the art.

The anti-FGFR4 monoclonal antibodies of the invention may be whole or an antigen-binding fragment of the antibody that specifically binds to an FGFR4 polypeptide, preferably a native sequence FGFR4 polypeptide. Furthermore, in a preferred embodiment the monoclonal antibody is as lab number mAb BT53 having recognition of a FGFR4 protein.

In one non-limiting embodiment the monoclonal antibody is produced by a hybridoma cell line, such that the antibody or functional fragment thereof binds to a FGFR4 protein or a fragment thereof. In one embodiment, the monoclonal antibody is of a murine IgG1, kappa chain isotype.

More specifically, the monoclonal antibody of the invention comprises a heavy chain variable region (HCVR) and a light chain variable region (LCVR), wherein said HCVR comprises: a) a peptide at CDRH1, b) a peptide at CDRH2, c) a peptide at CDRH3, and wherein said LCVR comprises: a) a peptide at CDRL1, b) a peptide at CDRL2, and c) a peptide at CDRL3.

Human and Humanized Antibodies

The murine monoclonal antibodies of the present invention can be humanized to reduce the immunogenicity for use in humans. Humanized forms of non-human (e.g., murine) antibodies are chimeric immunoglobulins, immunoglobulin chains or fragments thereof (such as, Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues, which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al. (1986) Nature 321:522; Riechmann et al. (1988) Nature 332:323; and, Presta (1992) Curr. Op. Struct. Biol. 2:593).

Methods for humanizing non-human antibodies are well known in the art. An example approach is to make mouse-human chimeric antibodies having the original variable region of the murine monoclonal antibodies, joined to constant regions of a human immunoglobulin. Chimeric antibodies and methods for their production are known in the art. See, e.g., Cabilly et al. European Patent EP0125023 (published Nov. 14, 1984); Taniguchi et al., European Patent EP0171496 (published Feb. 19, 1986); Morrison et al., European Patent Application EP0173494 (published Jan. 18, 1986); Neuberger et al., International Publication No. WO/1986/01533, (published Mar. 13, 1986); Kudo et al., European Patent Application EP0184187 (published Jun. 11, 1986); Robinson et al., International Publication No. WO/1987/002671 (published May 7, 1987); Liu et al. (1987) Proc. Natl. Acad. Sci. USA 84: 3439-3443; Sun et al. (1987) Proc. Natl. Acad. Sci. USA 84: 214-218; Better et al. (1988) Science 240: 1041-1043. These references are incorporated herein by reference. Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes.

Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al. (1986) Nature, 321:522-525; Riechmann et al. (1988) Nature, 332:323-327; Verhoeyen et al. (1988) Science, 239:1534-1536), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Pharmaceutical Compositions of Antibodies

In other embodiments there is provided a pharmaceutical composition including an antibody or fragment as described above together with a pharmaceutically acceptable carrier, diluent or excipient.

In the preparation of the pharmaceutical compositions comprising the antibodies described in the teachings herein, a variety of vehicles and excipients and routes of administration may be used, as will be apparent to the skilled artisan. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

The pharmaceutical compositions will generally comprise a pharmaceutically acceptable carrier and a pharmacologically effective amount of the antibodies, or mixture of antibodies.

The pharmaceutical composition may be formulated as powders, granules, solutions, suspensions, aerosols, solids, pills, tablets, capsules, gels, topical creams, suppositories, transdermal patches, and other formulations known in the art.

For the purposes described herein, pharmaceutically acceptable salts of the antibodies are intended to include any art-recognized pharmaceutically acceptable salts including organic and inorganic acids and/or bases. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. Thus, the antibodies or peptides, by themselves, such as being present as pharmaceutically acceptable salts, or as conjugates, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as solid formulations in appropriate excipients.

The pharmaceutical compositions will often further comprise one or more buffers (e.g., neutral buffered saline or phosphate buffered saline), carbohydrates (e.g., glucose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, adjuvants (e.g., aluminium hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

While any suitable carrier known to those of ordinary skill in the art may be employed in the compositions of this invention, the type of carrier will typically vary depending on the mode of administration. Antibody compositions may be formulated for any appropriate manner of administration, including for example, oral, nasal, mucosal, intravenous, intraperitoneal, intradermal, subcutaneous, and intramuscular administration.

For parenteral administration, the compositions can be administered as injectable dosages of a solution or suspension of the substance in a physiologically acceptable diluent with a pharmaceutical carrier that can be a sterile liquid such as sterile pyrogen-free water, oils, saline, glycerol, polyethylene glycol, or ethanol. Additionally, auxiliary substances, such as wetting or emulsifying agents, surfactants, pH buffering substances and the like can be present in compositions.

Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate. Antibodies can be administered in the form of a depot injection or implant preparation, which can be formulated in such a manner as to permit a sustained release of the active ingredient. An exemplary composition comprises antibody at 5 mg/ml, formulated in aqueous buffer consisting of 50 mM L-histidine, 150 mM NaCl, adjusted to pH 6.0 with HCl.

Typically, the compositions are prepared as injectables, either as liquid solutions or suspensions; solid or powder forms suitable for reconstitution with suitable vehicles, including by way example and not limitation, sterile pyrogen free water, saline, buffered solutions, dextrose solution, etc., prior to injection. The preparation also can be emulsified or encapsulated in liposomes or micro particles such as polylactide, polyglycolide, or copolymers.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles, as indicated above.

Alternatively, a pharmaceutical composition may be stored in a freeze-dried condition requiring only the addition of a sterile liquid carrier immediately prior to use.

The invention also relates to a pharmaceutical composition comprising the antibody of the invention in combination with at least one further antineoplastic agent. Said combination is effective, for example, in inhibiting abnormal cell growth.

Many antineoplastic agents are presently known in the art. In one embodiment, the antineoplastic agent is selected from the group of therapeutic proteins including but not limited to antibodies or immunomodulatory proteins. In another embodiment the antineoplastic agent is selected from the group of small molecule inhibitors or chemotherapeutic agents consisting of mitotic inhibitors, kinase inhibitors, alkylating agents, anti-metabolites, intercalating antibiotics, growth factor inhibitors, cell cycle inhibitors, enzymes, topoisomerase inhibitors, histone deacetylase inhibitors, anti-survival agents, biological response modifiers, anti-hormones, e.g. anti-androgens, and anti-angiogenesis agents.

In yet another embodiment the pharmaceutical composition comprises the antibody and an inhibitor of a member of the EGFR family, e.g. an EGFR, HER2, HER3 or HER4 inhibitor, particularly a HER2 inhibitor, e.g. an antagonistic antibody or a small molecule inhibitor.

The pharmaceutical composition of the invention can be used in human medicine and can be used also for veterinary purposes.

Uses for Anti-FGFR4 Antibodies

The anti-FGFR4 antibodies of the invention have various utilities. In one embodiment, anti-FGFR4 antibodies may be used in diagnostic or prognostic assays for FGFR4 expression on the surfaces of different cancer cells or exosomes, e.g., detecting its expression in specific cells, tissues, or serum. Various diagnostic and prognostic assay techniques known in the art may be used, such as competitive binding assays, direct or indirect sandwich assays and immunoprecipitation assays conducted in either heterogeneous or homogeneous phases (Zola, Monoclonal Antibodies: A Manual of Techniques, CRC Press, Inc. (1987) pp. 147-1581).

The antibodies used in the assays can be labeled with a detectable moiety. The detectable moiety should be capable of producing, either directly or indirectly, a detectable signal. Any method known in the art for conjugating the antibody to the detectable moiety may be employed, including those methods described by Hunter et al. (1962) Nature, 144:945; David et al. (1974) Biochemistry, 13:1014; Pain et al. (1981) J. Immunol. Meth., 40:219; and Nygren, J. Histochem. and Cytochem., 30:407 (1982).

"Detecting" refers to determining the presence, absence, or amount of an analyte in a sample, and can include quantifying the amount of the analyte in a sample or per cell in a sample.

"Diagnostic" refers to identifying the presence or nature of a pathologic condition. Diagnostic methods differ in their specificity and sensitivity. While a particular diagnostic method may not provide a definitive diagnosis of a condition, it suffices if the method provides a positive indication that aids in diagnosis.

"Immunoassay" refers to a method of detecting an analyte in a sample involving contacting the sample with an antibody that specifically binds to the analyte and detecting binding between the antibody and the analyte.

"Immunohistochemical" (abbreviated IHC) refers to specific binding agents, such as polyclonal and monoclonal antibodies, which recognize and mark antigens of interest, often by a chemical that shows that the agent has bound to the antigen of interest. An example of an IHC agent is an anti-FGFR4 monoclonal antibody.

The present invention relates to diagnostic assays, both quantitative and qualitative for detecting levels of FGFR4 polypeptide in cells, on cell membranes, and detectable in tissues and bodily fluids, including determination of normal and abnormal levels. Assay techniques that can be used to determine levels of a polypeptide, such as FGFR4, in a sample derived from a host are well-known to those of skill in the art. Such assay methods include, but are not limited to, radioimmunoassays, immunohistochemistry assays, in situ hybridization assays, competitive-binding assays, Western Blot analyses and enzyme-linked immunosorbent assays (ELISAs). Among these, ELISAs are frequently used to detect a gene's expressed protein in biological fluids. An ELISA assay initially comprises preparing an antibody specific to FGFR4, preferably a monoclonal antibody. In addition, a reporter antibody generally is prepared which binds specifically to FGFR4. The reporter antibody is attached to a detectable reagent such as a radioactive, fluorescent or enzymatic reagent, for example horseradish peroxidase enzyme or alkaline phosphatase.

The above tests can be carried out on samples derived from patients' bodily fluids (e.g., saliva, cerebrospinal fluid, semen, interstitial fluid, amniotic fluid, etc.) and tissue extracts (homogenates or solubilized tissue) such as from tissue biopsy and autopsy material. Levels of FGFR4, determined in cells and tissues from a patient suspected of suffering from cancer by measuring the polypeptide or by transcription levels, are compared to levels of FGFR4 in normal or control cells or tissues. Altered levels of FGFR4 measured in the patient as compared to levels in the same cells, tissues, or bodily fluids obtained from normal, healthy individuals (i.e., control samples) are indicative of cancer. By "altered levels" it is meant the assay detected a change (i.e., an increase or a decrease) in measured FGFR4 levels in a patient as compared to FGFR4 levels in the same normal cells or tissues. Detection of altered FGFR4 levels is useful in the diagnosis of various cancers including, but not limited to breast cancer, gastrointestinal cancer, pancreas cancer, prostate cancer, ovarian cancer, stomach cancer, endometrial cancer, salivary gland cancer, lung cancer, kidney cancer, colon cancer, colorectal cancer, thyroid cancer, bladder cancer, glioma, melanoma, hepatocellular carcinoma, gastric carcinoma, and lung cancer.

Further, monitoring of FGFR4 levels in a patient diagnosed with cancer is useful in determining the onset of metastases in cancers that have not yet metastasized and in determining the stage of the cancer. For example, detection of FGFR4 can be used in a method of monitoring cancer in a patient that has not metastasized for the onset of metastasis. In this method, a patient suffering from a cancer (e.g., breast cancer) that is not known to have metastasized is identified. FGFR4 levels in a sample from the patient are then measured. These measured FGFR4 levels are then compared with levels of FGFR4 from a normal control sample. A change in measured FGFR4 levels in the patient versus the normal control is associated with a cancer that has metastasized.

The stage of cancer in a patient suffering from, for example, breast cancer can also be determined. In this method a patient suffering from cancer is identified. FGFR4 levels in a sample of tissue from the patient are measured to establish a baseline FGFR4 level for said patient. FGFR4 levels in samples of the same tissue are then determined at subsequent time periods such as scheduled check-ups with the patient's physician. Measured FGFR4 levels are then compared with the baseline FGFR4 levels for the patient. In this method, an increase in measured FGFR4 levels in the patient versus baseline FGFR4 levels in the patient is associated with a cancer that is progressing and a decrease in measured FGFR4 levels versus baseline FGFR4 levels is associated with a cancer that is regressing or in remission. Increases in measured FGFR4 levels as compared to baseline FGFR4 levels established for the patient may also be indicative of metastases.

In one embodiment, FGFR4 immunohistochemistry functions as an "index diagnostic" to assign risk based on the presence of FGFR4 expression. Therefore, based on this and other parameters (e.g., size of lesion), one can determine whether or not different therapeutic modalities (i.e., chemotherapy, radiation therapy, surgery) should be used. In a related aspect, methods for monitoring progression of premalignancy into a malignant phenotype are disclosed. For example, by using serial sampling (i.e., biopsy) of the tissue and observing the state of FGFR4 expression in the lesions, one can determine whether or not the premalignancies are progressing in a way that would indicate whether therapeutic intervention is advised or is successful.

One aspect of the invention is a method to determine the likelihood of a group of cells to become cancerous e.g., for these cells or glands to become premalignancies or progress to cancerous lesions, or for determining the likelihood of a primary tumor to metastasize. The invention utilizes an agent, such as an antibody, that specifically binds to FGFR4 protein to assess levels of FGFR4 in tissue and cells. FGFR4 expression in cells and tissue may also be assessed using nucleic acid analysis, such as selective amplification, or hybridization methods. A level of FGFR4 greater than normal or control levels, indicates an increased likelihood that premalignant disease is present i.e., that the cells or tissues are premalignant, and/or that a primary tumor is likely to metastasize.

In another embodiment, the anti-FGFR4 antibodies are useful for a method of treatment of a disease, such as cancer. The method of the invention preferably includes the step of providing an antibody or FGFR4 antigen-binding fragment thereof, as described above, to a subject requiring said treatment.

Methods of immunotargeting cancer cells using antibodies or antibody fragments are well known in the art. U.S. Pat. No. 6,306,393, for instance, describes the use of anti-CD22 antibodies in the immunotherapy of B-cell malignancies, and U.S. Pat. No. 6,329,503 describes immunotargeting of cells that express serpentine transmembrane antigens. Antibodies described herein (including humanized or human monoclonal antibodies or fragments or other modifications thereof, optionally conjugated to cytotoxic or other agents) can be introduced into a patient such that the antibody binds to cancer cells and mediates the destruction of the cells and the tumor and/or inhibits the growth of the cells or the tumor.

Without intending to limit the disclosure, mechanisms by which such antibodies can exert a therapeutic effect may include complement-mediated cytolysis, antibody-dependent cellular cytotoxicity (ADCC) modulating the physiologic function of the tumor antigen, inhibiting binding or signal transduction pathways, modulating tumor cell differentiation, altering tumor angiogenesis factor profiles, modulating the secretion of immune stimulating or tumor suppressing cytokines and growth factors, modulating cellular adhesion, and/or by inducing apoptosis.

The anti-FGFR4 antibodies of the present invention may also act by reducing or blocking FGFR4-mediated signal transduction, reducing or blocking ligand binding, reducing or blocking cell proliferation, or reducing or blocking cell migration.

The antibodies can also be conjugated to toxic or therapeutic agents, such as radioligands, dyes, fluorescent and/or luminescent agents, or cytosolic toxins, and may also be used therapeutically to deliver the toxic or therapeutic agent directly to tumor cells. Moreover, in some embodiments of the invention, the labeled antibodies may be used to label cells in vivo or in vitro to determine levels of expression of FGFR4 protein. As such, the labeled cells may be directly or indirectly imaged via secondary methods that are applicable to each labeling agent.

By "treatment" herein is meant therapeutic, prophylactic, palliative, or suppressive treatment for the disease, disorder or undesirable condition. Treatment encompasses administration of the subject antibodies in an appropriate form prior to the onset of disease symptoms and/or after clinical manifestations, or other manifestations, of the disease to reduce disease severity, halt disease progression, or eliminate the disease. Prevention of the disease includes prolonging or delaying the onset of symptoms of the disorder or disease, preferably in a subject with increased susceptibility to the disease.

The therapeutic preparations can use non-modified antibodies or antibodies conjugated with a therapeutic compound, such as a toxin or cytotoxic molecule, depending on the functionality of the antibody. Generally, when non-modified antibodies are used, they will typically have a functional Fc region. By "functional Fc region" herein is meant a minimal sequence for affecting the biological function of Fc, such as binding to Fc receptors, particularly FcγR (e.g., Fcγ RI, FcγRII, and FcγRIII).

Without being bound by theory, it is believed that the Fc region may affect the effectiveness of anti-tumor monoclonal antibodies by binding to Fc receptors immune effector cells and modulating cell mediated cytotoxicity, endocytosis, phagocytosis, release of inflammatory cytokines, complement mediate cytotoxicity, and antigen presentation. In this regard, polyclonal antibodies, or mixtures of monoclonal antibodies will be advantageous because they will bind to different epitopes and thus have a higher density of Fc on the cell surface as compared to when a single monoclonal antibody is used. Of course, to enhance their effectiveness in depleting targeted cells, or where non-modified antibodies are not therapeutically effective, antibodies conjugated to toxins or cytotoxic agents may be used.

The antibody compositions may be used either alone or in combination with other therapeutic agents to increase efficacy of traditional treatments or to target abnormal cells not targeted by the antibodies. The antibodies and antibody compositions of the invention include PEGylated antibodies and/or pretargeting constructs of the antibodies. Combining the antibody therapy method with a chemotherapeutic, radiation or surgical regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well. Furthermore, treatment of cancer patients with the antibody with tumors resistant to chemotherapeutic agents might induce sensitivity and responsiveness to these agents in combination.

In one aspect, the antibodies are used adjunctively with therapeutic cytotoxic agents, including, by way of example and not limitation, busulfan, thioguanine, idarubicin, cytosine arabinoside, 6-mercaptopurine, doxorubicin, daunorubicin, etoposide, and hydroxyurea. Other agents useful as adjuncts to antibody therapy are compounds directed specifically to the abnormal cellular molecule found in the disease state. These agents will be disease specific.

The amount of the compositions needed for achieving a therapeutic effect will be determined empirically in accordance with conventional procedures for the particular purpose. Generally, for administering the compositions ex vivo or in vivo for therapeutic purposes, the compositions are given at a pharmacologically effective dose. By "pharmacologically effective amount" or "pharmacologically effective dose" is an amount sufficient to produce the desired physiological effect or amount capable of achieving the desired result, particularly for treating or retreating the disorder or disease condition, including reducing or eliminating one or more symptoms or manifestations of the disorder or disease.

As an illustration, administration of antibodies to a patient suffering from breast cancer provides a therapeutic benefit not only when the underlying disease is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

The amount administered to the subject will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but is not limited to, size and weight of the subject, the age and sex of the subject, the severity of the symptom, the stage of the disease, method of delivery of the agent, half-life of the agents, and efficacy of the agents. Stage of the disease to consider includes whether the disease is acute or chronic, relapsing or remitting phase, and the progressiveness of the disease. Determining the dosages and times of administration for a therapeutically effective amount is well within the skill of the ordinary person in the art.

For any compositions of the present disclosure, the therapeutically effective dose is readily determined by methods well known in the art. For example, an initial effective dose can be estimated from cell culture or other in vitro assays. For example, Sliwkowsky, M X et al. (1999) Semin. Oncol. 26. suppl. 12: 60-70 describes in vitro measurements of antibody dependent cellular cytotoxicity. A dose can then be formulated in animal models to generate a circulating concentration or tissue concentration, including that of the $IC_{50}$ as determined by the cell culture assays.

In addition, the toxicity and therapeutic efficacy are generally determined by cell culture assays and/or experimental animals, typically by determining a $LD_{50}$ (lethal dose to 50% of the test population) and $ED_{50}$ (therapeutically effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art, particularly given the detailed disclosure provided herein. Guidance is also found in standard reference works, for example Fingl and Woodbury, General Principles In: The Pharmaceutical Basis of Therapeutics pp. 1-46 (1975), and the references cited therein.

To achieve an initial tolerizing dose, consideration is given to the possibility that the antibodies may be immunogenic in humans and in non-human primates. The immune response may be biologically significant and may impair the therapeutic efficacy of the antibody even if the antibody is partly or chiefly comprised of human immunoglobulin sequences such as, for example, in the case of a chimeric or humanized antibody. Within certain embodiments, an initial high dose of antibody is administered such that a degree of immunological tolerance to the therapeutic antibody is established.

The tolerizing dose is sufficient to prevent or reduce the induction of an antibody response to repeat administration of the committed progenitor cell specific antibody.

Preferred ranges for the tolerizing dose are between 10 mg/kg body weight to 50 mg/kg body weight, inclusive. More preferred ranges for the tolerizing dose are between 20 and 40 mg/kg, inclusive. Still more preferred ranges for the tolerizing dose are between 20 and 25 mg/kg, inclusive.

Within these therapeutic regimens, the therapeutically effective dose of antibodies is preferably administered in the range of 0.1 to 10 mg/kg body weight, inclusive. More preferred second therapeutically effective doses are in the range of 0.2 to 5 mg/kg body weight, inclusive. Still more preferred therapeutically effective doses are in the range of 0.5 to 2 mg/kg, inclusive. Within alternative embodiments, the subsequent therapeutic dose or doses may be in the same or different formulation as the tolerizing dose and/or may be administered by the same or different route as the tolerizing dose.

For the purposes of this invention, the methods of administration are chosen depending on the condition being treated, the form of the subject antibodies, and the pharmaceutical composition.

Administration of the antibody compositions can be done in a variety of ways, including, but not limited to, continuously, subcutaneously, intravenously, orally, topically, transdermal, intraperitoneal, intramuscularly, and intravesically. For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, intraperitoneal administration can be accompanied by intravenous injections. Preferably the therapeutic doses are administered intravenously, intraperitonealy, intramuscularly, or subcutaneously.

The compositions may be administered once or several times. In some embodiments, the compositions may be administered once per day, a few or several times per day, or even multiple times per day, depending upon, among other things, the indication being treated and the judgment of the prescribing physician.

Administration of the compositions may also be achieved through sustained release or long-term delivery methods, which are well known to those skilled in the art. By "sustained release or" "long-term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the antibodies, such as biodegradable polymers described above; pumps, including peristaltic pumps and fluorocarbon propellant pumps; osmotic and mini-osmotic pumps; and the like.

The method of the invention contemplates the administration of single monoclonal antibodies and any antibody that recognizes the particular antigens recognized by these antibodies, as well as combinations, of different monoclonal antibodies. Two or more monoclonal antibodies may provide an improved effect compared to a single antibody. Alternatively, a combination of an antibody with an antibody that binds a different antigen may provide an improved effect compared to a single antibody. Additionally, contrast agents may be administered in combination with the antibodies in order to improve differential labeling of neoplastic cells or lesions. Such monoclonal antibodies cocktails may have certain advantages inasmuch as they contain monoclonal antibodies, which exploit different effector mechanisms or combine directly cytotoxic monoclonal antibodies with monoclonal antibodies that rely on immune effector functionality. Such monoclonal antibodies in combination may exhibit synergistic therapeutic effects.

Some embodiments of the present invention may also be used to isolate, collect, and/or otherwise purify components of tissues and/or cells. Some embodiments provide a method of isolating cells and/or byproducts, components, including components released from the cells (e.g., exosomes), and/or other portions of cells. In one embodiment, the anti-FGFR4 antibodies can be used in isolating cells and/or components of cells.

Antibody Kits

Antibody kits are provided which contain the necessary reagents to carry out the assays of the present invention. The kit may include one or more compartments, each to receive one or, more containers such as: (a) a first container comprising one of the components of the present invention described above; and (b) one or more other containers comprising one or more of the following: wash reagents, reagents capable of detecting presence of the antibody or peptide, and/or recombinant FGFR4 protein or fragments thereof as a control for detection or for a competitive assay. For example, in some embodiments, the kit can be configured as a cell isolation kit.

The containers allow one to efficiently transfer reagents from one compartment to another compartment such that the samples and reagents are not cross-contaminated, and the agents or solutions of each container can be added in a quantitative fashion from one compartment to another.

The kit typically contains containers, which may be formed from a variety of materials such as glass or plastic, and can include for example, bottles, vials, syringes, and test tubes. A label typically accompanies the kit, and includes any writing or recorded material, which may be electronic or computer readable form (e.g., disk, optical disc, or tape) providing instructions or other information for used of the contents of the kit. The label indicates that the formulation is used for diagnosing or treating the disorder of choice.

One skilled in the art will readily recognize that the disclosed antibodies of the present invention can be readily incorporated into one of the established kit formats, which are well known in the art.

All patent and literature references cited in the present specification are hereby incorporated by reference in their entirety.

The following examples are offered for illustrative purposes only, and are not intended to limit the scope of the present invention in any way.

EXAMPLES

Multiple murine hybridoma clones that secrete murine monoclonal antibodies that bind to the human FGFR4 protein were generated. As described in greater detail herein, these antibodies recognize (e.g., specifically bind) human FGFR4 in its native form or fragments thereof.

Commercially available reagents referred to in the examples were used according to manufacturer's instructions unless otherwise indicated. The following examples are offered for illustrative purposes only, and are not intended to limit the scope of the present invention in any way.

Example 1

General Hybridoma Production and Screening Protocol

The following protocols are used for general hybridoma production in the laboratory, as well as for screening and subcloning hybridomas.

General Hybridoma Fusion Protocol

Fusion Preparation:

3-4 Days Prior to Fusion

1) Two T-75 or one T-225 flask of myeloma cells, P3X653 (P3 cells), at $5 \times 10^5$ cell/ml (50 ml) in 10% C-DMEM were set up. Fresh media was added the day before fusion. In addition, during this timeframe, the animals that were used to generate desired lymphocytes for fusion received an intravenous booster injection. Moreover, any equipment that was to be used in harvesting tissue from the animals was autoclaved.

Day of the Fusion

On the day of fusion, Fusion Media was prepared as follows: DMEM (LTI) 128 ml, HAT (50×; Sigma) 4 ml, OPI (100×: Sigma) 2 ml, HEPES (1 M; Sigma) 2 ml, Glutamax I (100×; LTI) 2 ml, NCTC (Sigma) 20 ml, FBS (LTI) 40 ml, Pen/Strep (LTI) 2 ml, Nutridoma (BM) 2.0 ml. In addition, 50 ml of SF-DMEM with 0.5 ml of 1 M HEPES (DMEM/HEPES) was prepared. Thereafter, 9.5 ml of DMEM/HEPES and 0.5 ml DMSO was added to a conical tube (DMEM/HEPES/DMSO).

After preparation of the aforementioned media, the following were placed in a 37° C. water bath: 200 ml Fusion Media (FX-media), 40 ml DMEM/HEPES, 10 ml DMEM/HEPES/DMSO, and 1 ml aliquot of polyethylene glycol/DMSO mix (PEG/DMSO). In addition, eight flat bottom 96 well plates were labeled with fusion number, plate number, and date (e.g., FX03.5 8/31/07) Further, 50×HAT was suspended in 10 mL of SF-DMEM and 100×OPI was suspend in 10 mL sterile water.

Fusion

FIG. 1 illustrates the steps that can be employed in the fusion process. Initially, mice that have been previously immunized with an antigen (as described in greater detail below) were sacrificed and spleens were removed. Each spleen was placed in 10 ml DMEM/HEPES in a 100 mm cell culture dish. In addition, P3 cells were harvested and counted such that between 5 and 20×10$^7$ cells were used for fusion.

Once the spleens were placed in the cell culture dish, the splenocytes were removed by teasing the spleen and the resulting splenic cell suspension was placed in a 15 ml conical tube and large debris was allowed to settle for 2-3 minutes. At this time, the counted P3 cells were transferred to a 50 ml conical tube. In addition, the splenic-cell suspension was removed from the 15 ml conical tube, leaving behind the large debris and transferred to a new 15 ml conical tube. The splenic-cell suspension and the P3 cells were respectively pelleted by centrifugation.

Thereafter, the splenic cells (i.e., splenocytes) were washed with 10 ml of warm DMEM/HEPES, with gentle mixing to enable clots to stick to the pipet used to suspend the pelleted splenic cells. The P3 cells were also washed in 10 ml of DMEM/HEPES. The P3 cells and the splenic cells were again pelleted and respectively suspended in 5 ml each of warm DMEM/HEPES and mixed together in a 14 ml round-bottom tube (Falcon® 2059). The mixed-cell suspension was pelleted and the resulting supernatant was removed by aspiration. The resulting mixed-cell pellet was gently disrupted and incubated at 37° C. for 1-2 minutes.

In order to induce fusion of the splenic cells and P3 cells, 1 ml of 50% PEG/DMSO (Sigma) was added over 45-60 seconds with constant stirring and flicking. The cell suspension was then swirled at 37° C. for 45 seconds. After this incubation, the PEG was diluted out by adding 2 ml of warm DMEM/HEPES/5% DMSO over 2 minutes in the same manner as the PEG (i.e., stirring, flicking, and swirling at 37° C.). After this addition, the mixture was further diluted by adding 8 ml of DMEM/HEPES/DMSO over 2 minutes and the fused cells were incubated for 15 minutes at 37° C. After the incubation, the fused cells were pelleted and suspended in 160 ml of fusion medium with freshly added Nutridoma. The resulting mixture was plated at 200 µl/well and incubated in a plastic container at 37° C.

Limiting Dilution of Hybridomas

After incubation, the investigators performed two limiting dilutions prior to screenings to ensure that the screened cells were clones of a single origin. The following procedure was repeated twice, with the first limiting dilution using 20-HT medium and the second limiting dilution using 20-HY Medium.

Initially, 100 µl of media was added to each well of a flat-bottomed, 96-well tissue culture plate. Thereafter, 100 µl of culture from the fused cells (i.e., hybridomas) was added to the A1 well and mixed. After mixing, 100 µl from well A1 was transferred to well B1 and mixed. This same procedure was repeated along the first column of the cell culture plate up to well H1 (i.e., a series of two-fold dilutions along the first column of the 96-well plate). After this initial dilution, 100 µl of media was added to each well in the first column (A1-H1) to ensure that each well had 200 µl of media. Thereafter, using an eight-channel pipet, 100 µl of media and cells from the first column of the plate (wells A1-H1) was transferred to the second column of the plate (wells A2-H2). This same procedure was serially repeated to the twelfth column of the plate (wells A12-H12) to provide significant dilutions. Then, the plates were incubated at 37° C. for 7-10 before screening.

Screening of Fused Cells

Initially, two 384-well plates were coated with 25 µl per well of approximately 0.5 µg/ml of the protein of interest (e.g., native FGFR4 polypeptide comprising a sequence of SEQ ID NO:2) in coating buffer (50 mM Tris-Cl, pH 9.5). These two 384-well plates were incubated overnight at 4° C.

On the day of the screening, the coating comprising the protein of interest was removed and 50 µl per well of blocking buffer (1% BSA) was added and the plates were incubated for 30 min at 37° C. Thereafter, 25 µl from each well from the fusion plates was added and incubated for 1 hr at room temperature (RT). The wells were then washed three times with 50 µl/well of PBS-Tween (PBS-T). After the washing step, 25 µl of 1 µg/ml horseradish peroxidase-conjugated-GAM (an anti-mouse antibody of goat origin) Fc in PBS-T was added to each well and incubated for 1 hr at RT. Each well was then washed three times with 50 µl/well of PBS-T. After the washing step, 25 µl of OPD substrate (Pierce) with 0.1% hydrogen peroxide was added to each well and incubated for 15 min at RT. After incubation, 25 µl of STOP buffer (2 M sulfuric acid) was added to each well and the absorbance from each well was reach at 495 nM. Thereafter, the resulting data was analyzed using 384-well spreadsheet to determine which hybridomas produced antibodies that bind to the protein of interest.

Example 2

Experimental Methods

Production of Monoclonal Antibodies to FGFR4

Monoclonal antibodies (mAbs) were generated as previously described (Azorsa et al. (1999) *J Immunol Methods* 229:35-48) with the following modifications: Female Balb/c mice (6-8 weeks old) were injected with 3-5 million washed HeLa cells expressing FGFR4 (HeLa-FGFR4.cl21) in PBS via intraperitoneal injection 3 times at 2-week intervals, followed by injections of 3-5 million washed HeLa-FGFR4.cl21 in PBS for three consecutive days prior to sacrificing the mice. HeLa-FGFR4.cl21 had been previously transfected with a construct that expresses the native FGFR4 polypeptide (SEQ ID NO:1). Splenocytes were isolated and fused to the myeloma cell line P3×653 using PEG:DMSO (50:5, % v, Sigma-Aldrich), as described above. Fused cells were seeded in 96-well plates in DMEM:NCTC-109 (90:10, % v, Invitrogen, Carlsbad, Calif.) media supplemented with 20% FBS (Invitrogen), 2 mM Glutamax I (Invitrogen), 25 mM Hepes, 1×HAT (Sigma-Aldrich), Penicillin/Streptomycin, and 0.5× Nutridoma-CS (Roche, Branchburg, N.J.). Hybridoma colonies were screened by ELISA and were subcloned twice by limiting-dilution, as described above. In total, the inventors screened 768 hybridoma clones and subclones from the fusion experiments. Tissue culture supernatant from a hybridoma clone containing anti-FGFR4 mAbs termed BT53 was collected and stored with 0.02% sodium azide at 4° C.

A hybridoma line expressing monoclonal antibodies that specifically bind to human FGFR4 protein, as described above and below, was deposited with the American Type Tissue Culture Collection (ATCC; 10801 University Blvd, Manassas Va. 20110-2209) patent depository as original deposit under the Budapest Treaty and was given the following ATCC Accession No: clone BT53 (ATCC Patent Deposit Designation PTA-121019, deposited Feb. 21, 2014).

Screening of Hybridomas and Identification of BT53 Parental Clone

Initially, two 384-well flat-bottom ELISA plates were coated with 25 µl per well of approximately 0.5 µg/ml recombinant human FGFR4/Fc chimeric protein, which was purchased from R&D Systems (catalog number 685-FR) (SEQ ID NO. 2), in coating buffer (50 mM Tris-Cl, pH 9.5). The plates were incubated overnight at 4° C. The following day, the coating protein was removed and 50 µl of blocking buffer (1% Bovine Serum Albumin) was added to each well and the plates were incubated for 30 minutes at 37° C. After the incubation, 25 µl of supernatant from each hybridoma clone was added to each well of the ELISA plates and the plates were incubated for one hour at room temperature. After one hour, the plates were washed three times with 50 µl per well of PBS-Tween. Next, 25 µl of 1 µg/ml horseradish peroxidase goat-anti-mouse FC antibody (secondary antibody) was added to each well and incubated for one hour at room temperature. After one hour, the plates were washed three times with 50 µl per well of PBS-Tween. Then, 25 µl of OPD substrate from Pierce was added to each well with 0.1% hydrogen peroxide. The plates were then incubated for 15 minutes at room temperature. After completion of the incubation, 25 µl of STOP buffer (2M $H_2SO_4$) was added to each well and the optical density for each of the wells was read at 495 nm.

Once raw results were obtained for each of the 768 hybridoma clones and subclones tested, the values were normalized to the greatest value on the respective plates. In addition, the optical density was plotted out on a graph reflecting controls and different hybridoma supernatants tested.

After selection of hybridoma clones using the quantitative ELISA described above, a second set of ELISAs were performed. Specifically, these second ELISAs were performed only for qualitative purposes to further assess and confirm the binding of the monoclonal antibodies produced by the hybridoma clones to native FGFR4 polypeptide of SEQ ID NO:2.

Immunofluorescent Staining

Immunofluorescent microscopy was used to qualitatively validate the results from the ELISA experiments described above. In particular, HeLa-FGFR4.cl21 and 3T3-FGFR4.clS5 cells, which both express SEQ ID NO:1 (native FGFR4 polypeptide), were used to test specific binding of the monoclonal antibodies produced by the hybridoma clones. Cells from both cells lines were plated on chamber slides and allowed to grow to 50% confluency and fixed with 4% paraformaldehyde. Cells were immunostained with hybridoma supernatant containing anti-FGFR4 antibody (1:10 dilution) from multiple hybridoma clones followed by Cy3-conjugated goat anti-mouse secondary antibody (1:200, Jackson Immunoresearch, West Grove, Pa.). Cells were visualized using a fluorescent microscope and binding was qualitatively assessed.

Flow Cytometry

FGFR4 is highly expressed in rhabdomyosarcoma (RMS) tissue (Taylor et al. (2009) *J Clin Invest* 119:3395). Two RMS cell lines, RMS-RD and RMS Rh30, were analyzed by flow cytometry. In particular, cells from both lines were fixed and stained with primary antibodies of either negative control mouse IgG (mIgG), which recognizes mouse IgG or BT53 monoclonal antibodies, both of which were added at 1 µg/ml. After addition of the primary antibodies and incubation at room temperature for an hour, the cells were washed with PBS and divided into two groups. After washing, a first group of both types of cells were incubated with a first secondary antibody (goat anti-mouse IgG (GaM) antibodies conjugated to R-phycoerythrin (RPE)). A second group of both types of cells were incubated with a second secondary antibody (GAM antibodies conjugated to a near-infrared fluorochrome (DY-649)). All of the analyzed using a flow cytometer.

Example 3

Screening of Monoclonal Anti-FGFR4 Antibody

Figure 2:
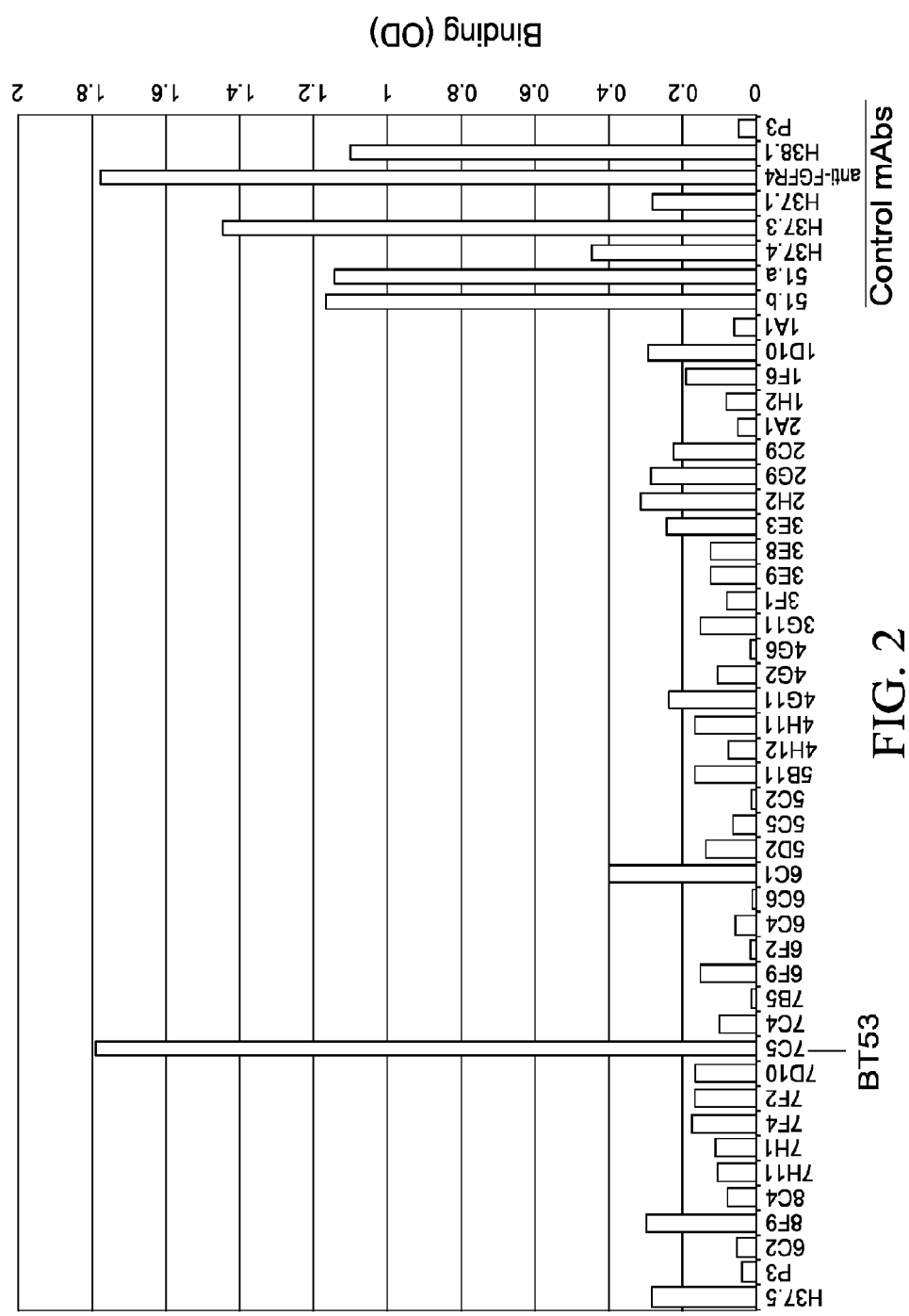
FIG. 2 depicts a bar graph that includes the Optical Density (OD) results from an ELISA screen of FGFR-binding capabilities of multiple hybridoma clones generated using methods described herein.

Initially, experiments were conducted to assess the specificity of the hybridoma lines generated as a result of the fusions described above. In particular, ELISAs were performed using the supernatant from 768 total hybridoma clones obtained by limiting dilutions (i.e., a total of eight 96-well plates). In these experiments, the wells of the respective ELISA plates were coated with the native FGFR4 polypeptide of SEQ ID NO:2 and each of the hybridoma clones was tested against control monoclonal antibodies, as illustrated in FIG. 2. Specifically, a variety of binding activities, as measured by optical density (OD), were noted in the multitude of hybridoma clones tested. However, antibodies from a hybridoma clone found in plate 7, well C5 exhibited the greatest OD, which translated to the greatest binding activity of all of the wells tested. This hybridoma clone from well 7C5 was further cloned through the limiting dilution to obtain a monoclonal population and was designated hybridoma BT53. As shown in FIG. 2, the monoclonal antibodies produced by the hybridoma clone in well 7C5 (i.e., a clone of hybridoma BT53) exhibited the greatest binding activity to SEQ ID NO:2, even compared to the control mAbs. Moreover, some of these quantitative OD values are also included in Table 1 under the ELISA 1 column. As such, hybridoma BT53 produced mAbs that not only successfully bound to native FGFR4 polypeptide, but did so with a greater binding activity compared to the control antibodies.

Next, qualitative experiments were performed to compare the 7C5 hybridoma clone (i.e., a clone of the BT53 hybridoma) to other hybridoma clones generated as a result of the fusion experiments detailed above. Initially, qualitative immunofluorescence experiments were conducted to assess the relative strength of binding activity of the 7C5 hybridoma clone compared to the other clones. First, HeLa-FGFR4.cl21 cells were exposed to supernatant from a multitude of hybridoma clones and binding was qualitatively assessed. As seen in Table 1, some clones exhibited some degree of binding to the cells; however, the 7C5 hybridoma cells exhibited the greatest binding to the HeLa-FGFR4.cl21 cells.

Additional experiments were performed to further validate this qualitative immunofluorescence data. As mentioned above, each of the clones included in Table 1 exhibit at least above background levels of binding activity to the HeLa-FGFR4.cl21 cells, with the BT53 hybridoma clone (7C5) exhibiting the greatest binding. However, as HeLa cells are human in origin, the administration of these cells during the vaccination process may result in the production of antibodies that generally recognize human peptides. In order to further validate the above-described data and to ensure that the mAbs produced by the hybridoma clones are binding the native FGFR4 polypeptide, the immunofluorescence experiments were repeated using 3T3-FGFR4.clS5 cells. These 3T3 cells are murine in origin and similarly express the entire native FGFR4 polypeptide (SEQ ID NO:1). As such, the hybridoma clones, which are murine in origin, should not bind to any antigens on the 3T3 cells except for the native FGFR4 polypeptide of SEQ ID NO:1. As illustrated in Table 1, the antibodies produced by the BT53 hybridoma clone were the only antibodies that yielded discernable binding activity against the transfected 3T3 cells, which further shows that the mAbs produced by the BT53 hybridoma strongly bind to only the native FGFR4 polypeptide.

A second, qualitative ELISA was repeated with a focus on the hybridoma clones listed in Table 1. In particular, the BT53 hybridoma clone (7C5) was the only clone to exhibit relative, qualitatively assessed binding to the FGFR4 polypeptide of SEQ ID NO:2. Moreover, the 7C5 clones were further subcloned and additional qualitative experiments were performed to ensure that the clonal population produced a single antibody that binds to native FGFR4 polypeptide. The qualitative ELISA and immunofluorescence data from these subcloned populations showed strong binding by all of the 7C5 subclones (data not shown), further illustrating the strong and specific binding activity of the mAbs produced by the BT53 hybridoma clone.

TABLE 1

Screening Results from anti-FGFR4 hybridoma clones.

| Clone Name | ELISA 1 (OD) | Immunofluorescence HeLa-FGFR4.cl21 | Immunofluorescence 3T3-FGFR4.ClS5 | ELISA 2 |
|---|---|---|---|---|
| 6C2 | 0.048 | + | − | − |
| 6F2 | 0.014 | + | − | − |
| 7C5 | 1.796 | ++ | ++ | ++ |
| 7D10 | 0.162 | + | − | − |
| 7F4 | 0.175 | + | − | − |
| 8F9 | 0.301 | +/− | − | − |

+ means binding detected,
− means no binding detected,
+/− means above background binding detected, and
++ means strong binding detected.

Next, the BT53 monoclonal antibody binding specificity data was further validated using flow cytometry. Specifically, two rhabdomyosarcoma (RMS) cell lines, RMS-RD and RMS Rh30, were analyzed by flow cytometry using mAbs from the BT53 hybridoma clone compared to an anti-mouse IgG antibody (i.e., a negative control). Moreover, two different secondary antibodies that recognize murine antibodies with different fluorochromes were used in these experiments. In addition, after performing these experiments, the resulting flow cytometry plots for a given cell type and secondary antibody were overlayed to provide a comparison between the BT53 mAbs and the negative control antibodies.

Figure 3:
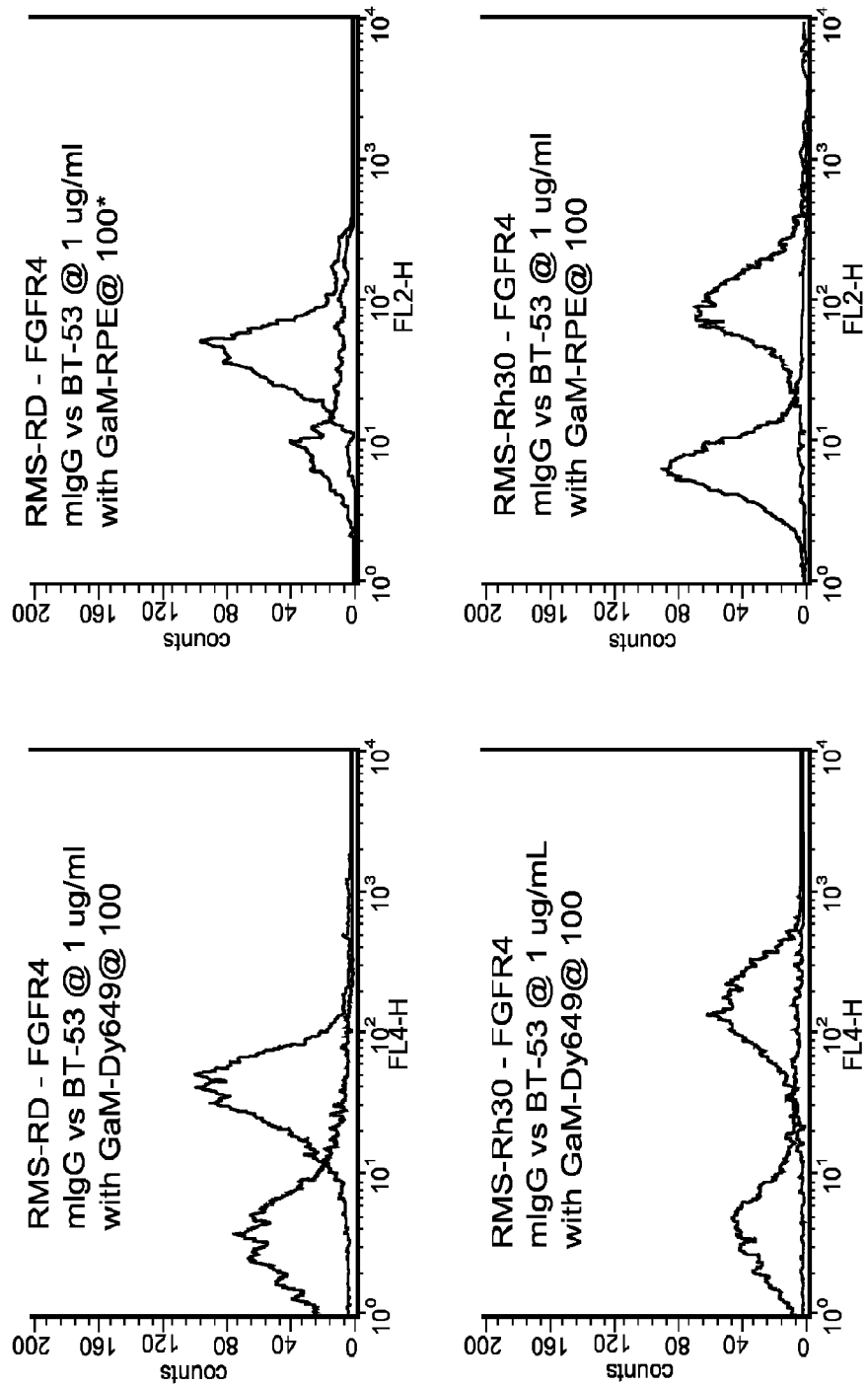
FIG. 3 depicts flow cytometry overlays illustrating the recognition of FGFR4 protein on two rhabdomyosarcoma cell lines using mAb BT53 and two different secondary antibodies with differing fluorochromes. In particular, on the two left overlays, the secondary antibody used Dy649, a near-infrared fluorochrome. The two right overlays used R-Phycoerythrin, which is read at a lesser wavelength. In the overlays, the solid plots positioned closer to zero on the x-axis reflect the cell populations stained with the negative control, an anti-mouse IgG antibody. The non-solid plots reflect the cell populations stained with the BT53 mAb.

Referring to FIG. 3, mAbs produced by the BT53 hybridoma line showed binding activity to both the RMS-RD and the RMS-Rh30 cells. First, the overlay plots on the left reflect both cells lines that had been stained with the Dy649 secondary antibody. In particular, the solid histograms (on the left side of the x-axis in both plots) reflect the negative control antibody, which shows little binding. Conversely, the hollow histograms (in the middle-right of the x-axis in both plots) reflect binding by the mAbs produced by the BT53 hybridoma line. Similarly, the overlay plots on the right reflect the same results using a different secondary antibody (R-PE). When viewed together, these overlay plots reflect that the mAbs produced by the BT53 hybridoma clone strongly and specifically bind to native FGFR4 polypeptide.

Having herein set forth the various embodiments of the present invention, it is anticipated that suitable modifications can be made thereto which will nonetheless remain within the scope of the invention. The invention shall therefore only be construed in accordance with the following claims below.

What is claimed is:

1. An isolated monoclonal antibody produced by hybridoma cell line BT53, ATCC accession number PTA-121019.

2. The monoclonal antibody of claim 1, wherein the antibody is labeled.

3. The monoclonal antibody of claim 2, wherein the antibody is labeled with one or more labels selected from the group consisting of a biotin label, a fluorescent label, an enzyme label, a coenzyme label, a chemiluminescent label, and a radioactive isotope label.

4. A method of making a monoclonal antibody, the method comprising providing hybridoma cell line BT53, ATCC accession number PTA-121019, which produces a monoclonal antibody specific for human native fibroblast growth factor receptor 4, and culturing the hybridoma cell line BT53 under conditions that permit the production of the monoclonal antibody.

5. The method of claim 4 and further comprising coupling a label to the monoclonal antibody.

6. The method of claim 5, wherein the label is selected from the group consisting of a biotin label, a fluorescent label, an enzyme label, a coenzyme label, a chemiluminescent label, and a radioactive isotope label.

7. The method of claim 4, wherein the monoclonal antibody specifically binds to the amino acid sequence of SEQ ID NO:2 and further comprising coupling a label to the monoclonal antibody with a fluorescent label, a chemiluminescent label, a biotin label, or a radioactive isotope label.

* * * * *